United States Patent
Castagliuolo et al.

(10) Patent No.: US 9,555,082 B2
(45) Date of Patent: Jan. 31, 2017

(54) **FORMULATIONS CONTAINING *SACCHAROMYCES BOULARDII* AND SUPEROXIDE DISMUTASE (SOD) TO CONTROL OBESITY**

(75) Inventors: Ignazio Castagliuolo, Desio (IT); Paola Brun, Desio (IT); Immacolata Busiello, Desio (IT); Niccolo Miraglia, Desio (IT)

(73) Assignee: Gnosis S.p.A., Desio (IT)

( * ) Notice: Subject to any disclaimer, the term of this patent is extended or adjusted under 35 U.S.C. 154(b) by 0 days.

(21) Appl. No.: 14/235,188

(22) PCT Filed: Aug. 2, 2012

(86) PCT No.: PCT/EP2012/065119
§ 371 (c)(1),
(2), (4) Date: Feb. 28, 2014

(87) PCT Pub. No.: WO2013/017650
PCT Pub. Date: Feb. 7, 2013

(65) Prior Publication Data
US 2014/0205581 A1    Jul. 24, 2014

(30) Foreign Application Priority Data
Aug. 3, 2011 (IT) ................ MI2011A1488

(51) Int. Cl.
*A01N 63/00* (2006.01)
*A61K 38/43* (2006.01)
*A61K 38/44* (2006.01)
*A61K 36/064* (2006.01)

(52) U.S. Cl.
CPC ........... *A61K 38/446* (2013.01); *A61K 36/064* (2013.01)

(58) Field of Classification Search
CPC .................. A01N 63/00; A61K 38/43
See application file for complete search history.

(56) References Cited

U.S. PATENT DOCUMENTS

| 8,591,880 B2 * | 11/2013 | Chou ............ A23K 1/009 424/780 |
| 2006/0008511 A1 * | 1/2006 | Lin et al. ............ 424/442 |
| 2012/0027891 A1 * | 2/2012 | Tobin ............ A23L 1/0067 426/62 |

FOREIGN PATENT DOCUMENTS

| WO | 2006041930 | 4/2006 |
| WO | 2011012655 | 2/2011 |
| WO | 2011045732 | 4/2011 |

OTHER PUBLICATIONS

Nedeva et al. (Cu/Zn superoxide dismutase in yeast mitochondria—a general phenomenon. FEMS Microbiology Letters 230 (2004) 19-25).*
Database WPI, Week 201031 Thomson Scientific, London, GB, XP002666780.
International Search Report issued in counterpart PCT Application No. PCT/EP2012/065119.
Written Opinion of International Searching Authority issued in counterpart PCT Application No. PCT/EP2012/065119.

* cited by examiner

*Primary Examiner* — Karen Cochrane Carlson
*Assistant Examiner* — Natalie Moss
(74) *Attorney, Agent, or Firm* — Amin Talati Upadhye LLP; George M. Carrera, Jr.; Adam D. Sussman (57) ABSTRACT

Disclosed is a composition containing *Saccharomyces cerevisiae* var *boulardii* and the enzyme superoxide dismutase.

2 Claims, 11 Drawing Sheets

° $p<0.05$ vs normal calorie diet
* $p<0.05$ vs high-calorie diet
§ $p<0.05$ vs high-calorie diet + Sb SOD

°$p<0.02$ vs VHF

VHF Sb and VHF Sb+SOD $p<0.02$ vs VHF: ONE-way ANOVA with Bonferroni's post test
VHF SOD and VHF Sb vs VHF Sb+SOD: ONE-way ANOVA with Newman-Keuls' post test

° $p<0.05$ vs normal calorie diet

\* $p<0.05$ vs high-calorie diet

Figure 9

°p<0.001 vs VHF

FORMULATIONS CONTAINING *SACCHAROMYCES BOULARDII* AND SUPEROXIDE DISMUTASE (SOD) TO CONTROL OBESITY

This application is a U.S. national stage of PCT/EP2012/065119 filed on Aug. 2, 2012, which claims priority to and the benefit of Italian Application No. MI2011A001488 filed on Aug. 3, 2011, the contents of which are incorporated herein by reference in their entirety.

The present invention relates to formulations useful as diet supplements containing the probiotic yeast *Saccharomyces boulardii* and the antioxidant enzyme superoxide dismutase. The formulations according to the invention are useful to reduce the risk of developing the metabolic syndrome correlated with obesity.

STATE OF THE ART

Obesity is defined as a condition of excess body fat, and is associated with a large number of dysfunctions, including cardiovascular disease (CVD) and non-insulin-dependent diabetes mellitus (NIDDM).

The prevalence of obesity and excess weight in adults, children and adolescents has grown rapidly in the last 30 years and continues to increase, leading to high social costs.

Obesity is generally viewed as the result of a combination of an excessive energy intake and a sedentary lifestyle, but although these factors are naturally important, it has recently been suggested that sub-optimal intestinal flora also has an influence (Tennyson Calif., Friedman G. Curr Opin Endocrinol Diabetes Obes. 2008 October; 15(5):422-7), while systemic metabolic complications are associated with the low-grade systemic inflammation that arises in obese individuals (Fantuzzi G., J Allergy Clin. Immunol. 2005; 115: 911-919, Bàckhed F, Ding H, Wang T, PNAS 2004; 101: 15718-15723).

Moreover, it has been demonstrated that some species of bacteria, such as the lactic acid producing bacteria in the species *L. gasseri*, *L. casei* and *L. acidophilus*, are able to reduce the weight increase in rats fed on a carbohydrate-rich diet (Kang J H, Yun S I, Park H O, J Microbiol. 2010 October; 48(5):712-4. Epub 2010 Nov. 3).

In support of these studies, products containing probiotic bacteria belonging to the genera *Lactobacillus* and *Bifidobacterium* have been described which are able to prevent or cure metabolic dysfunctions deriving from obesity (WO 2010146568; WO 2010091992; US 2008267933).

To date, in addition to the well described properties of probiotic bacteria, many articles in the scientific literature have described some beneficial effects on the health of a probiotic yeast, such as the inactivation of *Clostridium difficile* toxin A by the yeast *Saccharomyces boulardii* (Castagliuolo I, Riegler M F, Valenick L, LaMont J T, Pothoulakis C.-Infect Immun. 1999 January; 67(1):302-7) and the efficacy of *Saccharomyces boulardii* in preventing diarrhoea caused by antibiotic treatments or by infections due to intestinal pathogens (Surawicz C M, Elmer G W, Speelman P, McFarland L V, Chinn J, van Belle G.-Gastroenterology. 1989 April; 96(4):981-8; McFarland L V— World J Gastroenterol. 2010 May 14; 16(18):2202-22).

The enzyme superoxide dismutase (SOD), when administered parenterally, has proved effective in a number of inflammatory disorders (Carroll I M, et al. Am J Physiol Gastrointest Liver Physiol. 2007 October; 293(4):G729-38; Oku T, et al. Inflamm Bowel Dis. 2006 July; 12(7):630-40) reducing free radical formation and tissue damage.

Despite the number and detail of these studies, a composition based on probiotic yeasts which is able to prevent or counteract obesity and the correlated disorders has never been studied or proposed.

DESCRIPTION OF THE INVENTION

The present invention relates to a composition containing a probiotic yeast and an antioxidant, which is useful to reduce the risk of developing obesity and the metabolic syndrome correlated with it.

The probiotic yeast present in the composition, which is able to reduce the risk of developing the metabolic syndrome correlated with obesity, belongs to the genus *Saccharomyces*, and more preferably to the species *Saccharomyces cerevisiae* var. *boulardii* (hereinafter called Sb).

The antioxidant substance used in combination with the probiotic yeast Sb belongs to the class of antioxidant enzymes, and is more preferably the enzyme superoxide dismutase (hereinafter called SOD).

SOD is preferably prepared in gastroprotected form by means of conventional techniques and excipients. The effective dose of probiotic yeast is between $10^6$ and $10^9$ colony-forming units (CFU) per daily administration, preferably approx. $10^7$ CFU, while the effective dose of SOD is between 1 and 100 mg, preferably between 2 and 50 mg, and more preferably between 5 and 20 mg a day. A dose of approx. 10 mg a day is particularly preferred.

The yeast and the SOD could also be administered simultaneously, separately or sequentially: in such case, the two active ingredients need not be associated in a single dose unit, and could optionally be used in a product in kit form comprising separate dosage forms for the two active ingredients.

The efficacy of the diet supplement supplied by this invention has been evaluated by monitoring physical properties such as weight, abdominal fat accumulation and food intake, and measuring some biochemical parameters such as blood glucose and the pro-inflammatory cytokine level.

The efficacy of the composition according to the invention as a diet supplement was tested on a non-genetic murine obesity model obtained in male mice of the C57BL/6 line, which had received from the age of 4 weeks a normal or high-calorie diet supplemented daily with Sb and SOD or with the carrier alone.

During the 9-week administration of the diet supplement, the body weight and food intake were evaluated every week.

At the end of the administration period, the animals underwent the glucose tolerance test after fasting overnight; other animals were sacrificed to collect the peripheral blood needed to quantify the circulating cytokines and measure the accumulated abdominal fat.

The invention is described in greater detail in the examples below.

Example 1

Body Weight, Food Intake and Regulation of Body Fat

In order to evaluate the efficacy of the diet supplement consisting of the composition of Sb and SOD in regulating the physical properties influenced by obesity, male C57BL/6 mice (15.2±0.3 g) aged 4 weeks were divided into randomised groups to which a normal calorie diet (77% carbohydrate, 19% protein and 4% fat) or a high-calorie diet (VHF, 21% carbohydrate, 19% protein and 60% fat) was administered in the presence or absence of a daily supplement consisting of $10^7$ CFU of Sb (administered by gastric probe) and/or 10 mg of SOD extracted from yeast, purified and made gastro-resistant by microencapsulation up to a specific activity of 180000 U/g, and incorporated in the food. However, other methods of gastroprotection, such as the gliadin film medium or other equivalent techniques, would produce the same effect and can therefore be considered equivalent for the purposes of the present invention.

Diet and food supplements were administered continuously for a total of 9 weeks.

The food intake of the animals (Table) and their body weight were monitored weekly, while the accumulation of visceral fat was quantified after 9 weeks' diet supplementation.

Figure 2:
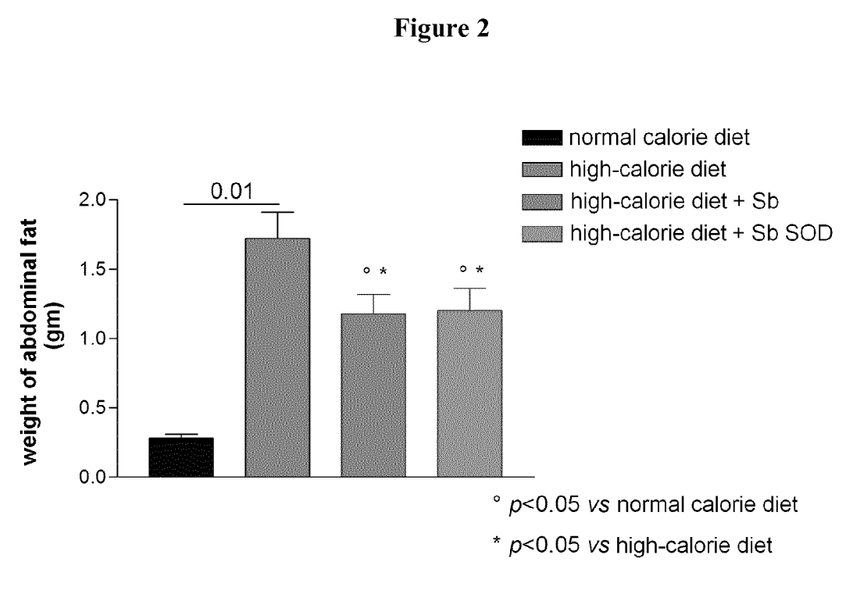
FIG. 2 depicts the accumulation of abdominal fat (gm) in the animal subjects of FIG. 1 after 9 weeks of supplementation.
Figure 2A:
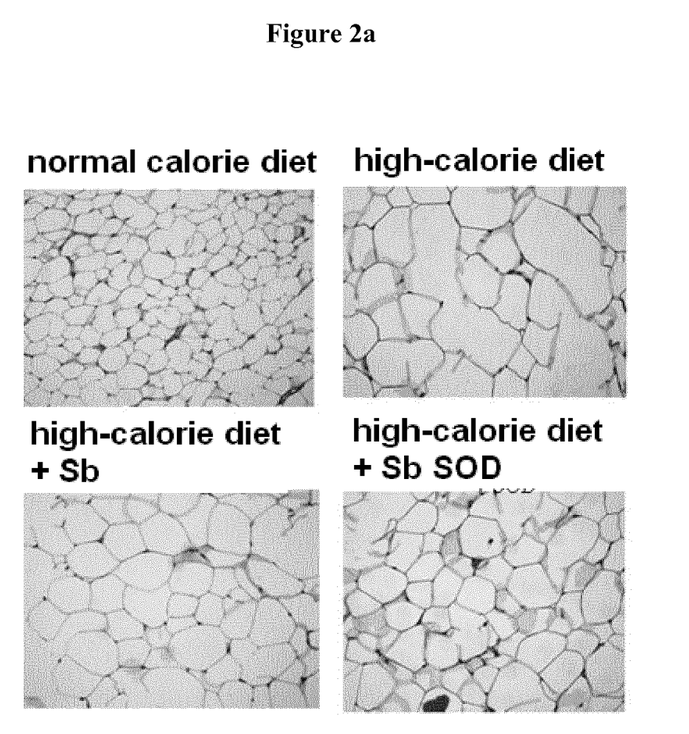
FIG. 2a depicts histology slides of the abdominal fat (gm) fixed in formalin obtained from the animal subjects of FIG. 1 after 9 weeks of supplementation.

At the end of the experimental period the animals were sacrificed and the abdominal fat was carefully collected, weighed and then fixed in formalin for the subsequent histological tests (FIG. 2a).

Figure 1:
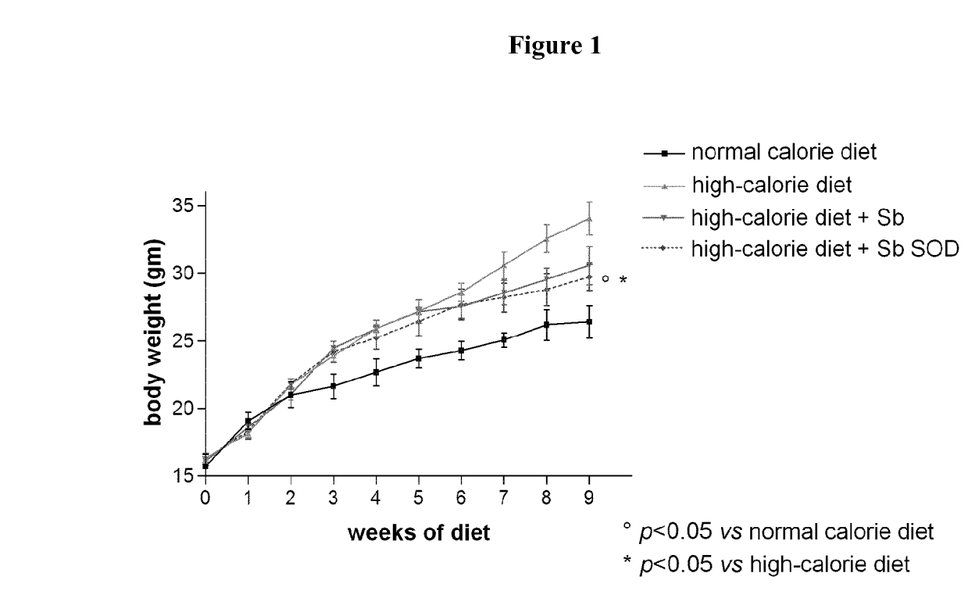
FIG. 1 depicts in one embodiment diet supplementation, in male mice of the C57BL/6 line, with *Saccharomyces cerevisiae* var *boulardii* (Sb) with or without superoxide dismutase enzyme (SOD) and reflects change in body weight (gm) over time up to 9 weeks.

Diet supplementation with Sb+SOD, but not with Sb alone, significantly reduces the weight increase associated with a high-calorie diet (FIG. 1). Moreover, the accumulation of adipose tissue at abdominal level was significantly reduced in the animals that received Sb alone and in those that received Sb in combination with SOD (FIGS. 2 and 2a).

TABLE

| Diet | Supplement | Food intake per mouse per day (g) | Calorie intake per mouse per day (kcal) |
|---|---|---|---|
| Normal calorie diet | no | 3.20 | 10.89 |
| High-calorie diet | no | 4.76 | 28.71 |
| High-calorie diet | Sb | 2.00 | 12.08 |
| High-calorie diet | Sb + SOD | 2.00 | 12.05 |

Example 2

Regulation of Biochemical Parameters in Obesity

In order to evaluate the efficacy of the diet supplement consisting of the composition of Sb and SOD in the metabolic complications associated with obesity after 9 weeks of the experiment described in example 1, the mice were subjected to an oral glucose loading test and a study of the cascade of signals induced by insulin in a target organ (liver).

To perform the oral glucose tolerance test, the blood glucose was determined after 18 hours' fasting and before administration of an oral glucose load (2 mg/g of body weight).

Figure 3A:
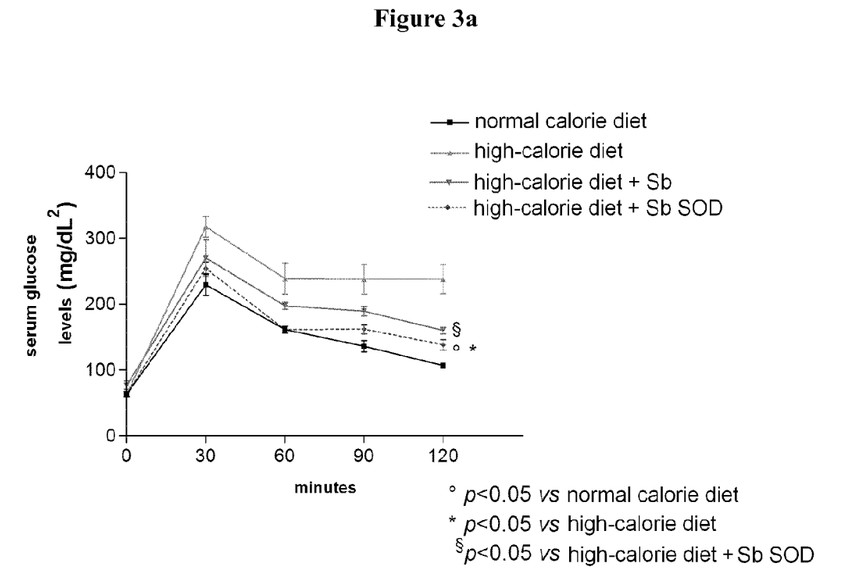
FIG. 3a depicts serum glucose levels (mg/dl) in an oral glucose tolerance test over time (min) in the animal subjects of FIG. 1 after 9 weeks of supplementation, determined after 18 hr fast, up to 120 min.
Figure 3B:
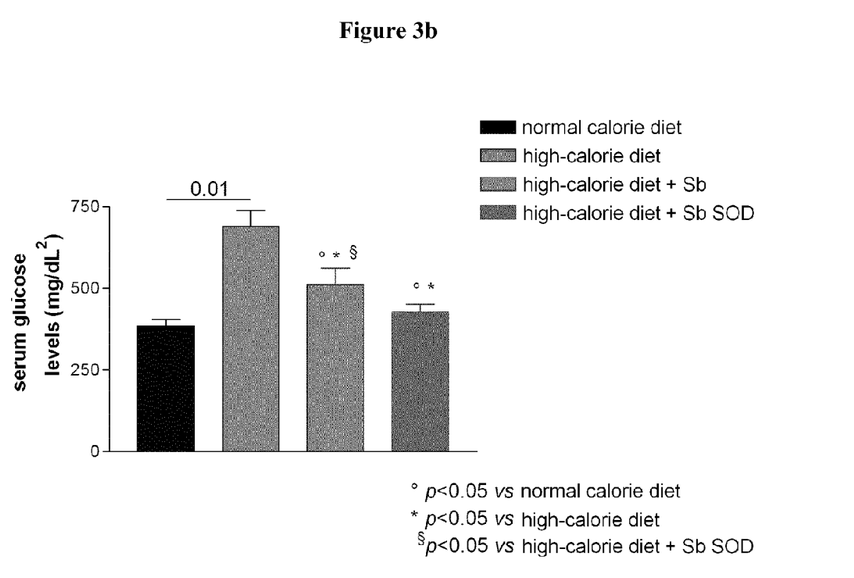
FIG. 3b depicts the glucose tolerance results (mg/dl) of FIG. 3a calculated as the area under the curve (AUC).

The blood glucose was then measured every 30 minutes for 120 minutes, and glucose tolerance was calculated as the area under the curve (AUC) (FIG. 3a and FIG. 3b).

To evaluate the functional state of the cascade of signals induced by insulin, an insulin load was administered intraperitoneally to the mice (10 U/Kg of weight). In this case the animals were sacrificed 5 minutes later, and liver samples were collected and frozen.

Figure 4:
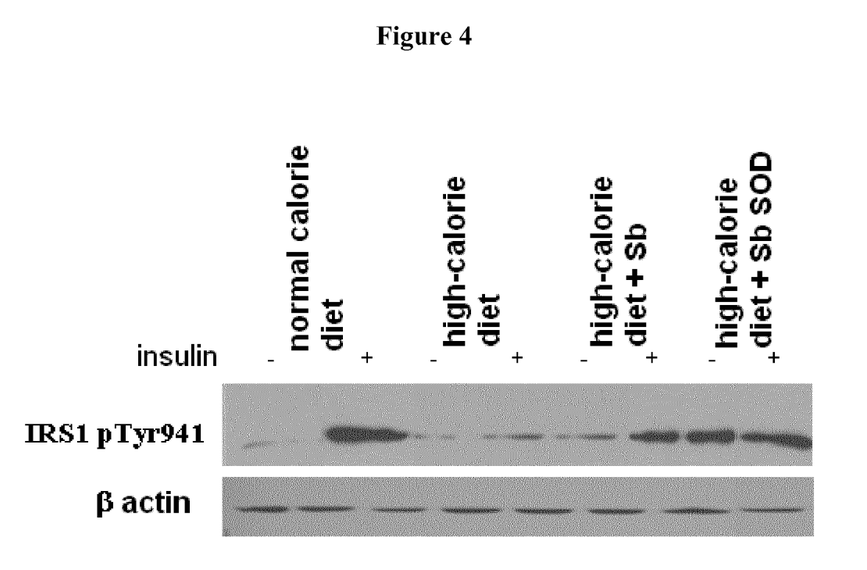
FIG. 4 depicts immunoblot gels to evaluate the phosphorylation level of the IRS1 (Insulin Receptor Substrate 1) protein in an insulin loading test administered i.p. in the animal subjects of FIG. 1 obtained from isolated liver samples of the test groups.

The total proteins were extracted from the liver samples and subjected to the immunoblot test to evaluate the phosphorylation level of the IRS1 (Insulin Receptor Substrate 1) protein (FIG. 4).

Under normal conditions, the bond between insulin and its receptor causes phosphorylation of the IRS1 protein on the Tyr941 residue, whereas in the case of the metabolic syndrome associated with obesity, this signal is reduced.

Supplementation with Sb or Sb+SOD using the same preparations and the same doses as in Example 1 reduced the extent of the post-glucose-load hyperglycaemia associated with obesity (FIGS. 3a and 3b). Co-administration of Sb and SOD caused a more marked reduction in post-load hyperglycaemia. Diet supplementation in obese mice with Sb and SOD restores the phosphorylation of IRS1 on the Tyr941 residue in response to a blood glucose load, therefore correcting the insensitivity of the target tissues to insulin (FIG. 4).

Example 3

Systemic Inflammation Caused by Obesity

Figure 5:
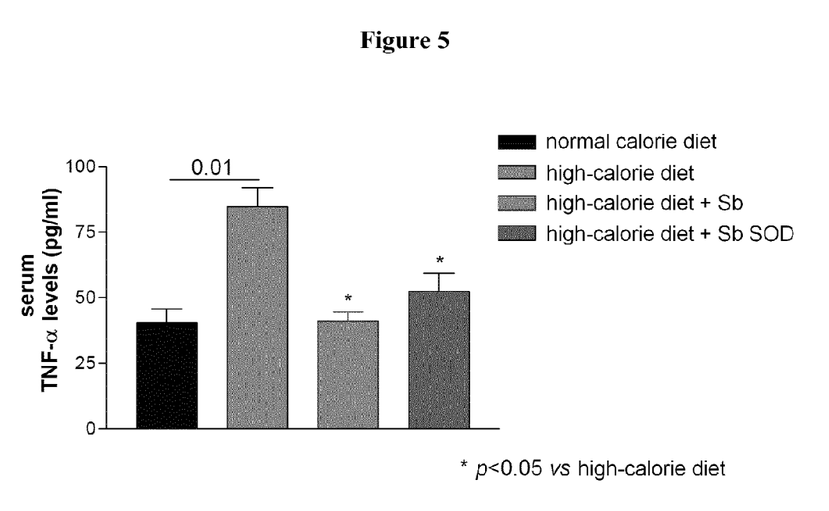
FIG. 5 depicts serum TNF-alpha levels (pg/ml) in the animal subjects of FIG. 1 after 9 weeks of supplementation, using ELISA assay.
Figure 6:
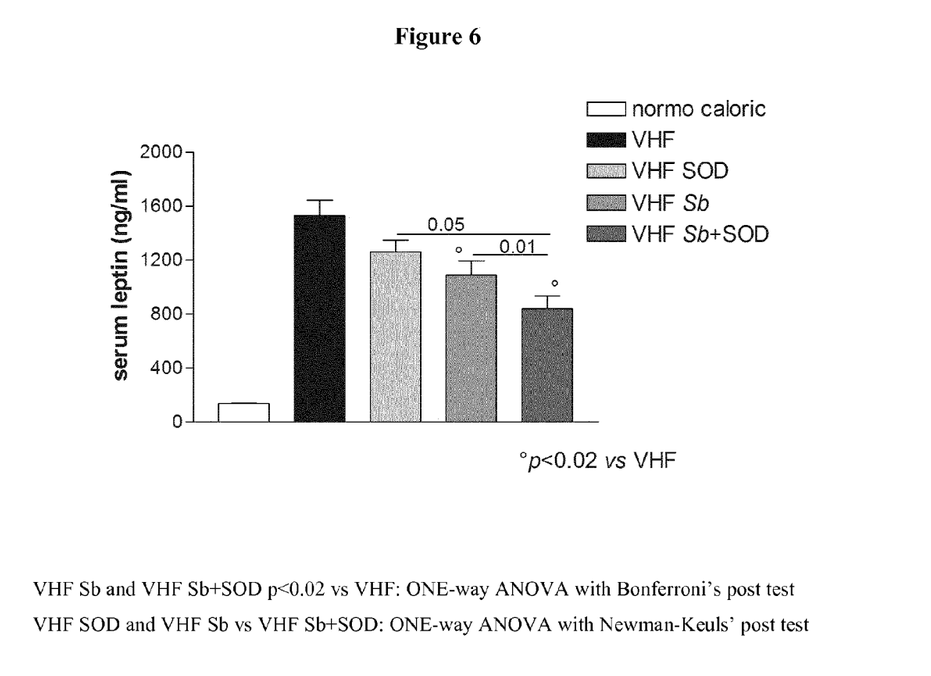
FIG. 6 depicts serum leptin levels (ng/ml) in the animal subjects of FIG. 1 after 9 weeks of supplementation, using ELISA assay.

To evaluate the efficacy of the diet supplement consisting of the composition of Sb and SOD on systemic inflammation, a common condition in obese individuals, after 9 weeks' diet supplementation a sample of circulating blood was taken to measure the circulating levels of pro-inflammatory cytokine (TNFα) and an adipokine (leptin). The assay was conducted on serum using the ELISA assay (FIG. 5 and FIG. 6).

In the case of obese animals an increase in the circulating levels of TNFα and leptin was observed, which contribute to the development of systemic complications. Diet supplementation with Sb or Sb+SOD using the same preparations and the same doses as in Example 1 significantly reduces the circulating levels of TNFα and leptin (FIG. 5 and FIG. 6). In particular, serum level of leptin, a pro-inflammatory adipokine derived from adipose tissue with a role in food taking regulation, is reduced by the supplementation with Sb+SOD at a significantly higher rate even if compared to Sb and SOD single supplementations (FIG. 6).

Example 4

Inflammatory State of the Intestinal Mucosa in Obesity

In order to evaluate the efficacy of the diet supplement consisting of the composition of Sb and SOD on the inflammatory condition of the mucosa associated with obesity after 9 weeks' diet supplementation, the animals were sacrificed so that a segment of ileum could be collected. The intestinal segments were homogenised in phosphate buffer to which a cocktail of protease inhibitors was added for the extraction of the total proteins. The homogenate was centrifuged at 13000× rpm for 10 min at 4° C., and the clarified supernatant was used to quantify the pro-inflammatory cytokines IL1-β and TNF-α by ELISA assay and to quantify glutathione (GSH), the most effective anti-oxidant natural compound. The cytokine levels were normalised to the total protein levels determined by the Bradford assay.

Figure 7:
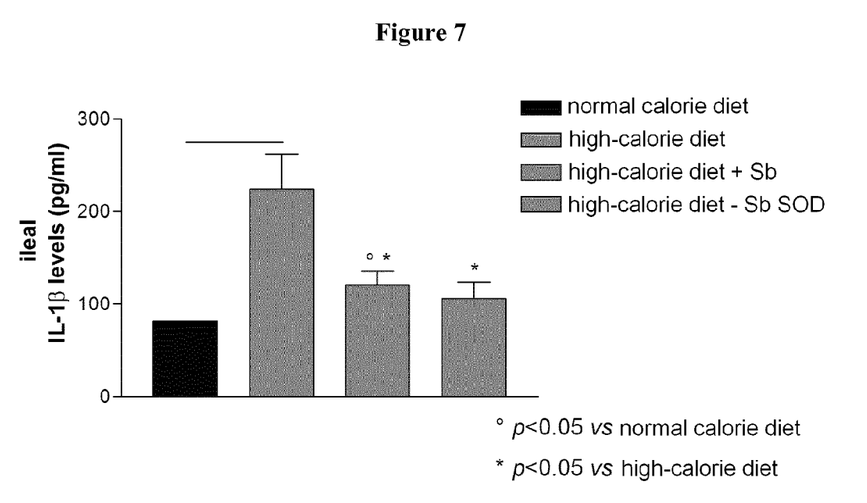
FIG. 7 depicts ileal IL-1beta levels (pg/ml) in the animal subjects of FIG. 1 after 9 weeks of supplementation obtained from homogenized ileal segments of the test groups., using ELISA assay.
Figure 8:
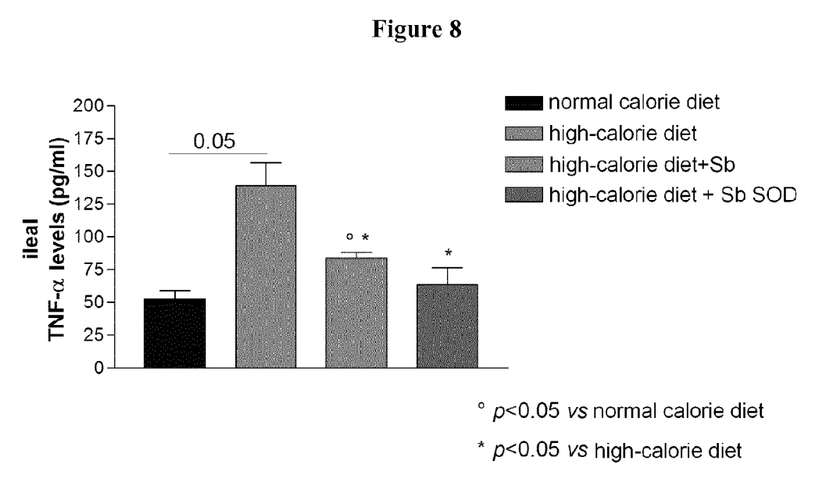
FIG. 8 depicts ileal TNF-alpha levels (pg/ml) in the animal subjects of FIG. 1 after 9 weeks of supplementation obtained from homogenized ileal segments of the test groups., using ELISA assay.

In the case of obese individuals, an increase in the levels of IL1-β and TNFα, which contribute to the development of systemic complications, is observed in the intestinal mucosa. Diet supplementation with Sb or co-administration of Sb and SOD using the same preparations and the same doses as in Example 1 induces a significant reduction in both cytokines (FIGS. 7 and 8). FIGS. 7 and 8 clearly show that only co-administration of Sb and SOD restores IL1-β and TNFα in the intestinal mucosa to comparable values with the control mice.

Figure 9:
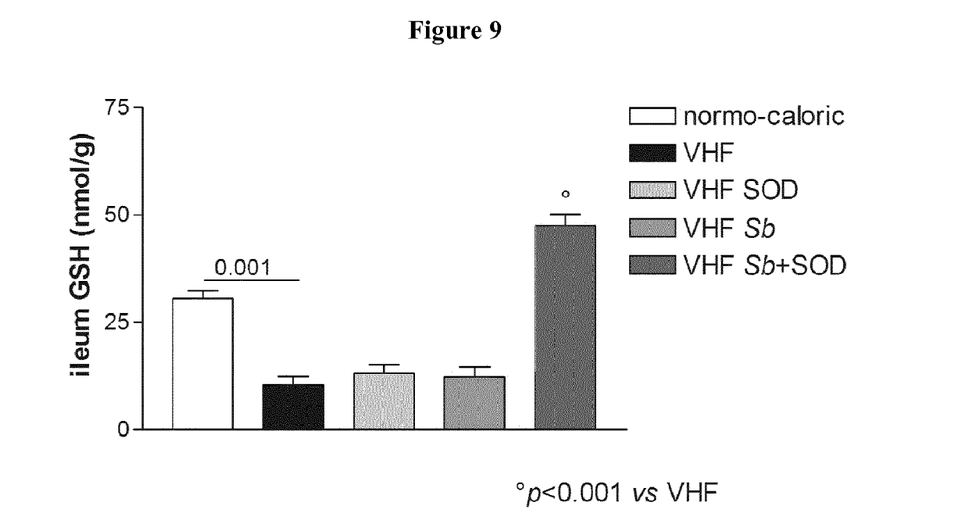
FIG. 9 depicts ileum glutathione levels (nmol/g) in the animal subjects of FIG. 1 after 9 weeks of supplementation obtained from homogenized ileal segments of the test groups., using ELISA assay.

Glutathione (GSH), which has a powerful anti-oxidant activity and that can be related to an anti-inflammatory role at the mucosal level, shows a significant decrease in the ileum of the obese animals. Its level is surprisingly increased in case of a supplementation with Sb+SOD while single supplementations with either Sb or SOD alone are not effective (FIG. 9).

The invention claimed is:

1. A method for reducing the risk of developing metabolic dysfunctions related to obesity, comprising administering to an individual in need thereof an effective amount of a composition containing *Saccharomyces cerevisiae* var *boulardii* together with an additional amount of microencapsulated extracted superoxide dismutase enzyme, wherein the additional amount of microencapsulated extracted superoxide dismutase enzyme is present in an amount from about 1 mg to about 100 mg.

2. A method for reducing one or more of weight increase, food intake, body fat accumulation, or the systemic inflammatory condition connected with obesity, comprising administering to an individual in need thereof an effective amount of a composition containing *Saccharomyces cerevisiae* var *boulardii* together with an additional amount of microencapsulated extracted superoxide dismutase enzyme, wherein the additional amount of microencapsulated extracted superoxide dismutase enzyme is present in an amount from about 1 mg to about 100 mg.

* * * * *